United States Patent
Friedman et al.

(10) Patent No.: US 7,538,230 B2
(45) Date of Patent: May 26, 2009

(54) LETROZOLE PRODUCTION PROCESS

(75) Inventors: Oded Friedman, Yehiel (IL); Boris Freger, Beer Sheva (IL); Olga Etlin, Beer Sheva (IL); Julia Ditkovitch, Beer Sheva (IL); Edna Danon, Meitar (IL); Yana Seryi, Beer Sheva (IL); Guy Davidi, Even Yehuda (IL); Oded Arad, Rehovot (IL); Joseph Kaspi, Givatayim (IL)

(73) Assignee: Chemagis Ltd., Bnei Brak (IL)

( * ) Notice: Subject to any disclaimer, the term of this patent is extended or adjusted under 35 U.S.C. 154(b) by 522 days.

(21) Appl. No.: 11/273,276

(22) Filed: Nov. 14, 2005

(65) Prior Publication Data

US 2007/0112202 A1 May 17, 2007

(51) Int. Cl.
*C07D 249/08* (2006.01)
(52) U.S. Cl. .................................................. 548/262.2
(58) Field of Classification Search ............... 548/262.2
See application file for complete search history.

(56) References Cited

U.S. PATENT DOCUMENTS

| | | | |
|---|---|---|---|
| 4,978,672 A | 12/1990 | Bowman et al. | |
| 5,073,574 A | 12/1991 | Lang | |
| 5,378,721 A | 1/1995 | Lang | |
| 5,473,078 A * | 12/1995 | Bowman et al. | ......... 548/262.2 |
| 2006/0128775 A1 | 6/2006 | Patel et al. | |

FOREIGN PATENT DOCUMENTS

| | | |
|---|---|---|
| CN | 1754876 A | 4/2006 |
| WO | WO 2004/076409 A2 | 9/2004 |
| WO | WO 2005/047269 A1 | 5/2005 |

* cited by examiner

*Primary Examiner*—Golam M M Shameem
*Assistant Examiner*—Susannah Chung
(74) *Attorney, Agent, or Firm*—Leydig, Voit & Mayer, Ltd.

(57) ABSTRACT

Provided is a method for preparing letrozole, which includes reacting an activated bis-(4-cyanophenyl)-methane with a triazole to produce letrozole, and, optionally, purifying the letrozole. Also provided are highly pure letrozole, and a method of purifying letrozole, which method includes precipitating letrozole, e.g., by selective precipitation from a reaction mixture and/or by subjecting the letrozole to one or more crystallizations.

17 Claims, No Drawings

LETROZOLE PRODUCTION PROCESS

BACKGROUND OF THE INVENTION

Letrozole, the active ingredient in the product Femara®, is a nonsteroidal aromatase inhibitor, which has the chemical name 4-[α-(4-cyanophenyl)-1-(1,2,4-triazolyl)-methyl]-benzonitrile, and the following structural formula (I):

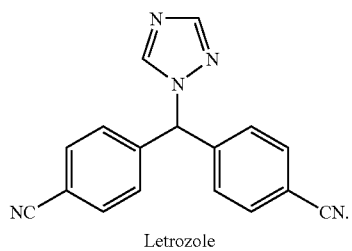

Letrozole

Letrozole was developed for treatment of advanced breast cancer in postmenopausal women with disease progression following anti-estrogen therapy, especially for first-line treatment of postmenopausal women with hormone receptor positive or hormone receptor unknown locally advanced or metastatic breast cancer.

The endosynthesis of estrogen in postmenopausal women is mediated by the aromatase enzyme, which converts androstenedione and testosterone and other androgens into estradiol and estrone. Letrozole inhibits the biosynthesis of estrogen from adrenal androgens (thus causing reduction in estrogen levels) by competitive binding to the heme portion of the cytochrome P450 subunit of aromatase. This binding reduces estrogen production, which significantly lowers serum estrogens. The suppression of estrogen may decrease the stimulatory effects of estrogen on tumor growth in estrogen-responsive tumors. Letrozole reportedly exerts no clinically relevant detectable effect on the synthesis of adrenal corticosteroids and aldosterone or on thyroid function.

U.S. Pat. No. 4,978,672 ("the '672 patent") describes a process for preparing letrozole by reacting α-bromo-4-tolunitrile with 1,2,4-triazole to produce 4-[1-(1,2,4-triazolyl)methyl]-benzonitrile, and reacting the product with 4-fluorobenzonitrile to obtain letrozole.

U.S. Pat. No. 5,473,078 ("the '078 patent") describes a method of preparing 4-[1-(1,2,4-triazolyl)methyl]benzonitrile by refluxing a solution of α-bromo-4-tolunitrile with 1,2,4-triazole for 15 hours in a mixture of acetonitrile and chloroform. The intermediate is purified by chromatography on silica gel, eluting with chloroform and isopropanol, and then reacted with 4-fluorobenzonitrile and potassium tert-butoxide in DMF, to obtain letrozole. An exemplary process described in the '078 patent is generally depicted in Scheme 1.

Scheme 1

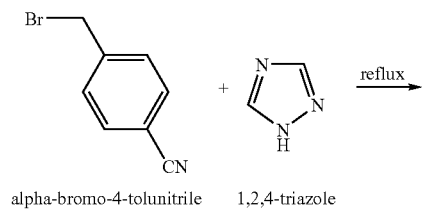

alpha-bromo-4-tolunitrile    1,2,4-triazole

-continued

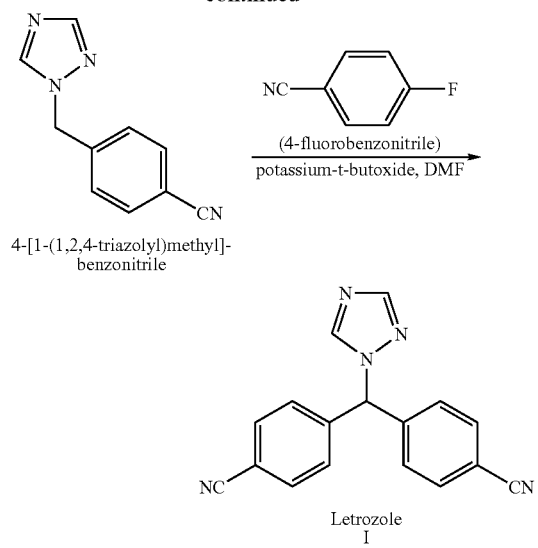

The processes described in the '672 and '078 patents are problematic in that the first step produces considerable quantities of the unwanted isomer 4-[1-(1,3,4-triazolyl)-methyl]-benzonitrile, which has the following structural formula (II):

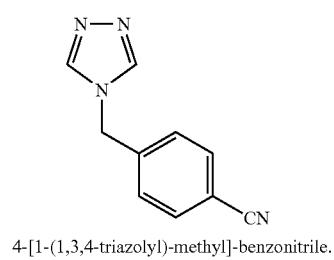

4-[1-(1,3,4-triazolyl)-methyl]-benzonitrile.

Methods for addressing the problem of forming the 1,3,4-isomer (II) have been reported. For instance, WO 2005/047269 describes a precipitation process for separating the desired intermediate (4-[1-(1,2,4-triazolyl)methyl]-benzonitrile) from the 1,3,4-isomer (II). However, this method requires an extra step of purification at an intermediate stage in the synthesis, which can be impractical on an industrial scale. Alternatively, WO 2004/076409 ("the '409 application") describes a regioselective process for preparing letrozole, which includes reacting 4-halomethyl-benzonitrile with 4-amino-1,2,4-triazole followed by deamination and reaction with 4-fluorobenzonitrile. The process described in the '409 application is generally depicted in Scheme 2.

Scheme 2

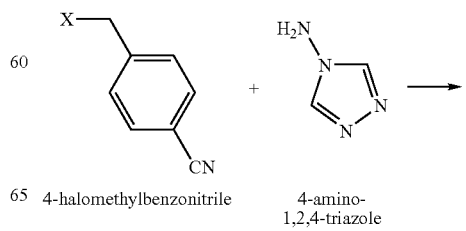

4-halomethylbenzonitrile    4-amino-1,2,4-triazole

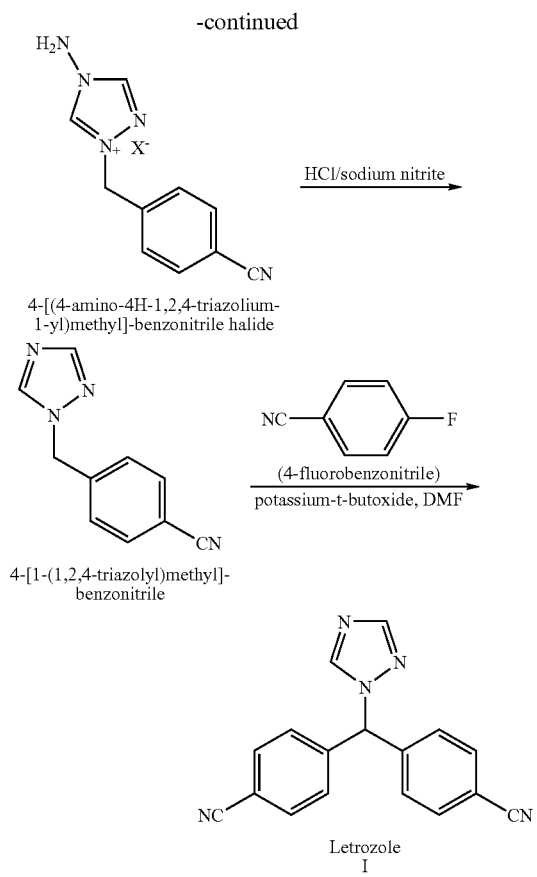

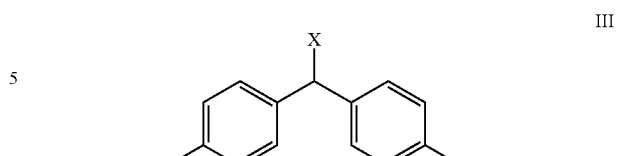

While the process described in the '409 application is said to avoid formation of the 1,3,4-isomer (II), the synthetic route requires an additional step of deamination with sodium nitrite and hydrochloric acid. Further, reacting sodium nitrite with hydrochloric acid produces nitrous acid, which is toxic and can create an explosion hazard. As such, the process described in the '409 application has limited potential for industrial application.

In view of the foregoing, there is a need for an improved, industrially viable process for obtaining highly pure letrozole. The present invention provides such a process.

BRIEF SUMMARY OF THE INVENTION

The present invention provides a method for preparing letrozole, which includes reacting an activated bis-(4-cyanophenyl)-methane with a triazole to produce letrozole. The activated bis-(4-cyanophenyl)-methane preferably includes a leaving group, which can be displaced by the triazole, to produce letrozole. The activated bis-(4-cyanophenyl)-methane can include, e.g., halo-bis-(4-cyanophenyl)-methane derivatives (wherein the leaving group is a halogen) and sulfonate esters of bis-(4-cyanophenyl)-methanol (wherein the leaving group is a sulfonate ester).

In one embodiment, the present invention provides a method of preparing letrozole, which method comprises reacting a triazole with an activated bis-(4-cyanophenyl)-methane of the formula (III):

wherein X is a leaving group, to produce letrozole. Suitable leaving groups can include, for example, halogens and sulfonate esters.

Compounds of formula III can be obtained, e.g., from bis-(4-cyanophenyl)-methanol, e.g., via chlorination to obtain chloro-bis-(4-cyanophenyl)-methane or via bromination to obtain bromo-bis-(4-cyanophenyl)-methane. Such halogenation reactions can be achieved, e.g., by reacting bis-(4-cyanophenyl)-methanol with an acid (e.g., by bubbling in a gaseous acid or adding an by aqueous acid to the bis-(4-cyanophenyl)-methanol in an organic solvent). The halo-bis-(4-cyanophenyl)-methane can be used without any purification step and reacted directly with a triazole (e.g., sodium 1,2,4-triazole, or 1,2,4-triazole under basic conditions) in a suitable solvent (e.g., an organic solvent).

The present invention further provides a method for purifying letrozole, which preferably includes selectively precipitating letrozole to remove at least a portion of an isoletrozole impurity therefrom. In one embodiment, crude letrozole produced in accordance with the synthesis method of the invention is purified by selective precipitation from the reaction mixture containing a water-immiscible solvent, by adding a mixture of water and a water-miscible solvent to the reaction mixture and selectively precipitating the letrozole therefrom. Alternatively (or additionally) the crude letrozole can be purified by crystallization from an organic solvent. Highly pure letrozole can thus be obtained in accordance with the present invention, without using column chromatography.

DETAILED DESCRIPTION OF THE INVENTION

The present invention provides a method for preparing letrozole, which includes reacting an activated bis-(4-cyanophenyl)-methane with a triazole to produce letrozole, which can purified without column chromatography. Preferably, the activated bis-(4-cyanophenyl)-methane comprises a leaving group, which can be displaced by the triazole, to produce letrozole. Suitable activated bis-(4-cyanophenyl)-methane intermediates can include, e.g., halo-bis-(4-cyanophenyl)-methane derivatives (wherein the leaving group is a halogen) and sulfonate esters of bis-(4-cyanophenyl)-methanol (wherein the leaving group is a sulfonate ester).

In one embodiment, the present invention provides a method of preparing letrozole, wherein the method includes reacting a triazole with an activated bis-(4-cyanophenyl)-methane of the formula (III):

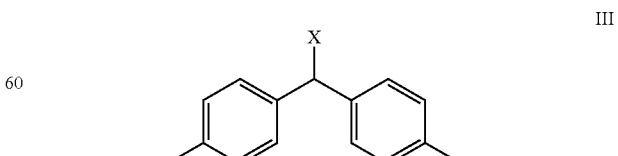

wherein X is a leaving group, to produce letrozole. Suitable leaving groups can include, for example, halogens (e.g., chloride, bromide, and the like) and sulfonate esters (e.g., methanesulfonate, p-toluene sulfonate, and the like).

Preferably, the activated bis-(4-cyanophenyl)-methane is a halogenated bis-(4-cyanophenyl)-methane. Such compounds can be produced, e.g., by halogenating bis-(4-cyanophenyl)-methanol (e.g., a compound of formula III, wherein X is OH) or a suitable analog thereof to produce a compound of formula III, wherein X is a halogen. For instance, the activated bis-(4-cyanophenyl)-methane can be produced by chlorinating bis-(4-cyanophenyl)-methanol to produce chloro-bis-(4-cyanophenyl)-methane, or by brominating bis-(4-cyanophenyl)-methanol to produce bromo-bis-(4-cyanophenyl)-methane. Alternatively, the activated bis-(4-cyanophenyl)-methane can be produced by sulfonating bis-(4-cyanophenyl)-methanol (e.g., by reaction with a suitable sulfonyl chloride) to produce a compound of formula III, wherein X is a sulfonate ester.

The triazole used in accordance with the present invention can include, e.g., 1,2,4-triazole, a salt thereof (e.g., a metal salt of the triazole such as, e.g., 1,2,4-triazole sodium salt), or a precursor of 1,2,4-triazole, which is capable of displacing the leaving group.

The letrozole produced in accordance with the present invention can be readily purified without the use of column chromatography. In this regard, it has been found that the major by-product produced in accordance with the synthesis method of the invention is 4-[α-(4-cyanophenyl)-1-(1,3,4-triazolyl)methyl]-benzonitrile (hereinafter "isoletrozole"), which has the structural formula (IV):

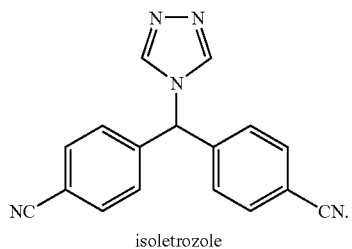

isoletrozole

Letrozole and isoletrozole are structurally similar, have similar physical properties, e.g., pKa, and are not readily separable from each other using conventional extraction techniques. However, it has been found that the letrozole can be readily separated from the isoletrozole by selectively precipitating and/or crystallizing the letrozole, which allows for facile purification of the letrozole.

In one embodiment, the letrozole is purified by selectively precipitating letrozole from a reaction mixture containing letrozole. In another embodiment, the letrozole is purified by crystallization from an organic solvent and, optionally, further purified by one or more subsequent crystallizations.

Highly pure letrozole can thus be obtained using the synthesis method of the present invention. Preferably, the letrozole produced in accordance with the invention has a purity of greater than about 95%. More preferably, the letrozole produced in accordance with the invention has a purity of at least about 98.5%, e.g., at least about 99.5%, e.g. at least about 99.7%. Alternatively, it is preferred that the letrozole produced in accordance with the invention contains isoletrozole in an amount of less than about 1 wt %, for example, isoletrozole at less than about 0.5 wt %, e.g., isoletrozole at less than about 0.2 wt %.

The synthesis method of the present invention can include, e.g.:

preparing a halo-bis-(4-cyanophenyl)-methane from bis-(4-cyanophenyl)-methanol (wherein "halo" refers to a halogen atom);

isolating the halo-bis-(4-cyanophenyl)-methane;

optionally purifying the halo-bis-(4-cyanophenyl)-methane by crystallization or precipitation;

converting the isolated halo-bis-(4-cyanophenyl)-methane into letrozole; and purifying the letrozole thus obtained by selective precipitation from the reaction mixture as described herein (e.g., by adding a mixture of water and a water-miscible solvent) and/or by crystallization.

The halo-bis-(4-cyanophenyl)-methane can be produced by any suitable method. Preferably, the halo-bis-(4-cyanophenyl)-methane is produced by reacting bis-(4-cyanophenyl)-methanol with an acid, to produce the halo-bis-(4-cyanophenyl)-methane, and, optionally isolating the product. The acid can be introduced as a gas (e.g., a gaseous acid) or as an aqueous solution. Exemplary acids, which can be used for producing the halo-bis-(4-cyanophenyl)-methane, can include hydrochloric acid, hydrobromic acid, and combinations thereof. Alternatively, bis-(4-cyanophenyl)-methanol can be reacted with sulfuric acid and a halogen-containing salt (e.g., a metal halide) to produce a halo-bis-(4-cyanophenyl)-methane.

Any suitable solvent can be used for reacting bis-(4-cyanophenyl)-methanol with an acid, to produce the halo-bis-(4-cyanophenyl)-methane. Suitable solvents can include, e.g., one or more solvents selected from the group consisting of toluene, ethyl benzene, xylenes, N,N-dimethylformamide (DMF), and combinations thereof. The halo-bis-(4-cyanophenyl)-methane is preferably produced by reacting bis-(4-cyanophenyl)-methanol with an acid in a solvent that comprises toluene. Preferably, the halo-bis-(4-cyanophenyl)-methane is selected from the group consisting of chloro-bis-(4-cyanophenyl)-methane and bromo-bis-(4-cyanophenyl)-methane.

Accordingly, the synthesis method of the present invention includes halogenating bis-(4-cyanophenyl)-methanol, to produce a halo-bis-(4-cyanophenyl)-methane, reacting the halo-bis-(4-cyanophenyl)-methane directly with a triazole to produce letrozole, and purifying the letrozole, wherein the halo-bis-(4-cyanophenyl)-methane is optionally isolated prior to reaction with the triazole. Preferably, the bis-(4-cyanophenyl)-methanol is either chlorinated to obtain chloro-bis-(4-cyanophenyl)-methane, or brominated to obtain bromo-bis-(4-cyanophenyl)-methane, either by bubbling in a gaseous acid or by introducing an aqueous acid in an organic solvent. The crude product thus produced can be obtained in high purity and yield, and can be subsequently reacted with a triazole, e.g., sodium 1,2,4-triazole or 1,2,4-triazole, under basic conditions, in at least one organic solvent without any purification step, to produce letrozole. The crude letrozole can be purified as described herein, without using chromatography, to obtain a substantially pure product.

Preferably, the halo-bis-(4-cyanophenyl)-methane is prepared by a process that includes: reacting bis-(4-cyanophenyl)-methanol with an acid, e.g., by bubbling in a gaseous acid or by introducing an aqueous acid to the bis-(4-cyanophenyl)-methanol in an organic solvent, optionally in the presence of a salt; and isolating the halo-bis-(4-cyanophenyl)-methane product from the reaction mixture. The organic solvent used in this halogenation reaction is preferably selected from the group consisting of toluene, ethyl benzene, xylenes, DMF, and the like, and mixtures thereof. More preferably, the halogenation solvent includes toluene. The halo-bis(4-cyanophenyl)-methane is preferably chloro-bis-(4-cyanophenyl)-methane or bromo-bis(4-cyanophenyl)-methane. The acid is preferably selected from the group consisting of sulfuric acid, hydrochloric acid, hydrobromic acid, and the like. The salt is preferably selected from the group consisting of zinc chloride, sodium bromide, sodium chloride, and the like. An exemplary process for producing the halo-bis-(4-cyanophenyl)-methane includes reacting bis-(4-cyanophenyl)-methanol with a mineral acid such as, e.g., hydrochloric acid, in toluene and in the presence of zinc chloride, to produce chloro-bis-(4-cyanophenyl)-methane.

The synthesis method of the present invention preferably includes reacting a halo-bis-(4-cyanophenyl)-methane with a triazole such as, e.g., 1,2,4-triazole or a salt thereof, in the presence of at least one base and at least one organic solvent, to produce crude letrozole; and purifying the crude letrozole. In a preferred embodiment, the present invention provides a process for preparing letrozole, which includes: reacting a halo-bis-(4-cyanophenyl)-methane with triazole or sodium triazole in at least one organic solvent and in the presence of a base, to produce crude letrozole; purifying the crude letrozole by selective precipitation from the reaction mixture; and further purifying the letrozole by crystallization.

The reaction with a triazole can be performed in any suitable solvent, which can include, e.g., one or more solvents selected from the group consisting of toluene, ethyl benzene, xylenes, N,N-dimethylformamide (DMF), N,N-dimethylacetamide (DMA), dimethyl sulfoxide (DMSO), and combinations thereof. More preferably, the solvent used in the displacement reaction is selected from the group consisting of toluene, DMF, and combinations thereof. An exemplary solvent can include a mixture DMF and toluene, e.g., in a ratio of about 2:3 DMF:toluene (vol./vol.).

Any suitable base can be used in the reaction with triazole. Suitable bases can include, e.g., one or more bases selected from the group consisting of sodium hydroxide, potassium hydroxide, sodium carbonate, potassium carbonate, sodium bicarbonate, potassium bicarbonate, and the like, and combinations thereof. Preferably, the base includes potassium carbonate.

The crude letrozole can be purified by any suitable process, which preferably includes selective precipitation, e.g., in the presence of at least two liquid phases, or crystallization from a solvent, as described herein.

An exemplary process of the present invention for synthesizing letrozole from bis-(4-cyanophenyl)-methanol is depicted in Scheme 3.

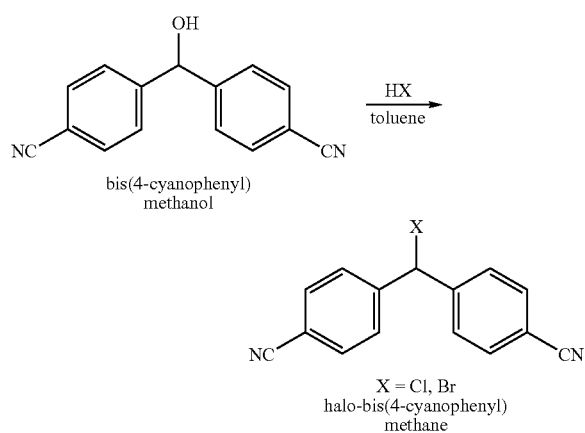

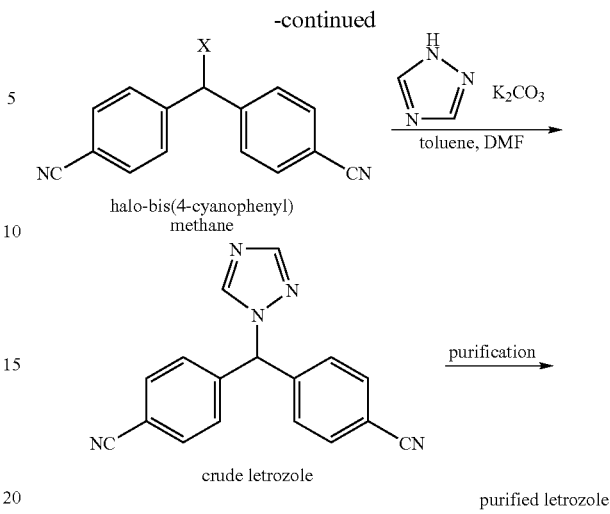

An exemplary process of the present invention for producing letrozole from chloro-bis-(4-cyanophenyl)-methane is depicted in scheme 4.

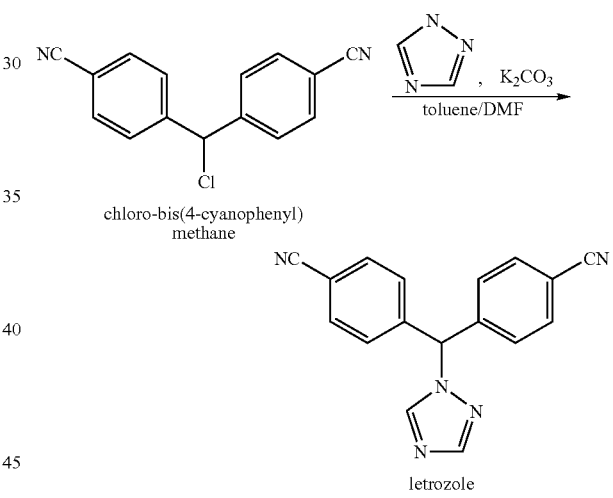

The present invention further provides a method for purifying letrozole, which contains isoletrozole as an impurity and, optionally, one or more additional impurities. The method of purifying letrozole in accordance with the invention preferably includes selectively precipitating letrozole to remove at least a portion of isoletrozole and, optionally, one or more additional impurities therefrom. In accordance with the present invention, the letrozole can be selectively precipitated from a reaction mixture, which preferably includes an organic solvent. The method of selectively precipitating letrozole from a reaction mixture in accordance with the present invention allows letrozole to be easily separated from its isomer isoletrozole. Alternatively (or additionally), the letrozole can be purified, e.g., after isolation from the reaction mixture, by crystallization from a solvent.

An exemplary process for selectively precipitating letrozole includes:

optionally adding an acid (e.g., an organic acid) to a reaction mixture containing letrozole and preferably containing one or more water immiscible solvents; adding water and at least one water-miscible solvent to the reaction mixture to produce a multi-phase system comprising at least two (e.g., immiscible) liquid solvent phases and at least one solid phase, wherein the solid phase comprises letrozole;

heating the system and allowing the mixture to cool, to precipitate purified letrozole; and, isolating the crystals.

By way of further example, the process for selectively precipitating letrozole from a reaction mixture in accordance with the invention can include:

optionally adding an organic acid to a reaction mixture containing letrozole and preferably containing one or more water immiscible solvents;

adding water and a water-miscible solvent to the reaction mixture after completion of the reaction to form a suspension (a three-phase system);

heating to an elevated temperature and allowing the reaction mixture to cool; and isolating the resulting crystalline solid; and, washing and drying the crystalline solid, optionally under reduced pressure.

In accordance with the present invention, an acid (e.g., an organic acid) optionally can be added to stabilize the system. An exemplary acid, which can be added to the system in accordance with the invention, is acetic acid.

In accordance with the purification method of the present invention, letrozole can be selectively precipitated as a solid (and collected) from a multi-phase system, which is preferably a three-phase system comprising two liquid phases and one solid phase, wherein the solid phase comprises letrozole. Such a multi-phase system can include, for example, a water-immiscible solvent, a water-miscible solvent and water, which, together with the letrozole, form a three-phase system, which includes a suspension of a solid tetrozole phase and two liquid phases.

Preferably, the multi-phase system is a three-phase system, which includes a water-miscible solvent in which isoletrozole is soluble, a water-immiscible solvent in which other impurities (e.g., starting materials such as, e.g., chloro-bis(4-cyanophenyl)-methane or bromo-bis(4-cyanophenyl)-methane) are soluble, and a solid phase that contains letrozole, wherein the letrozole is insoluble in the water-miscible and the water-immiscible solvent phases.

Any suitable water-immiscible solvent can be used for selectively precipitating letrozole in accordance with the present invention. Suitable water-immiscible solvents can include, for example, one or more solvents selected from the group consisting of toluene, ethyl benzene, xylenes, and the like, and mixtures thereof. Preferably, the water-immiscible solvent includes toluene.

Any suitable water-miscible solvent can be used for selectively precipitating letrozole in accordance with the present invention. Suitable water-miscible solvents can include, for example, one or more solvents selected from the group consisting of acetonitrile, acetone, N,N-dimethylformamide (DMF), N,N-dimethylacetamide (DMA), dimethyl sulfoxide (DMSO), and the like, and combinations thereof. Preferably, the water-miscible solvent includes DMF.

For instance, the letrozole can be selectively precipitated from a reaction mixture containing letrozole, e.g., a reaction mixture obtained in accordance with the synthesis method of the invention, by selectively precipitating the letrozole from a solvent system containing DMF, toluene and water in a ratio of from about 1:1:1 (vol./vol./vol.) DMF:toluene:water to about 1:1:2 (vol./vol./vol.) DMF:toluene:water, e.g., about 1:1:1.6 (vol./vol./vol.) DMF:toluene:water. The solvent system, from which the letrozole is selectively precipitated, can be obtained, e.g., by adding one or more solvents to a reaction mixture, which preferably contains a water-immiscible solvent, to produce a solvent system containing two liquid phases in which letrozole can exist in the form of a separate (third) solid phase. Thus, by adding a suitable amount of water and a water-miscible solvent to a reaction mixture (already comprising a water-immiscible solvent and a water-miscible solvent) after completion of the reaction, purified letrozole may be conveniently and easily obtained by selective precipitation.

For example, DMF and water can be added to a reaction mixture containing DMF, toluene or a combination thereof, to produce a solvent system having a desired solvent ratio (e.g., about 1:1:1.6 (vol./vol./vol.) DMF:toluene:water), from which the letrozole can be selectively precipitated. By way of further example, letrozole can selectively precipitated from a reaction mixture, e.g., produced by reacting chloro-bis-(4-cyanophenyl)-methane or bromo-bis-(4-cyanophenyl)-methane with 1,2,4-triazole or the sodium salt thereof, in a mixture of DMF and toluene, e.g., from about 1:9 (vol./vol.) DMF:toluene (e.g., containing about 10% DMF and about 90% toluene) to about 2:3 (vol./vol.) DMF:toluene (e.g., containing about 40% DMF and about 60% toluene), by adding suitable quantities of water and a water-miscible solvent, and selectively precipitating letrozole from the resulting system in accordance with the present invention.

Preferably, the solvent used in the reaction (from which letrozole is selectively precipitated) includes a water-miscible solvent, which is preferably selected from the group consisting of acetonitrile, acetone, N,N-dimethylformamide (DMF), N,N-dimethylacetamide (DMA) and dimethyl sulfoxide (DMSO). More preferably, DMF is used as the water-miscible solvent in the reaction mixture from which letrozole is selectively precipitated in accordance with the invention.

The letrozole can be precipitated in the form of crystals, which can be isolated (e.g., by filtration). If desired, the crystals further can be washed with a suitable solvent, which can include, e.g., one or more solvents selected from the group consisting of acetone, methanol, water, N,N-dimethylformamide (DMF), toluene, and combinations thereof. Preferably, the solvent used for washing the letrozole crystals includes water.

The multi-phase system from which the letrozole is selectively precipitated can be heated to any suitable temperature. In one embodiment, the system is heated to a temperature of from about 25° C. to about 60° C., e.g., about 30° C. For instance, letrozole can selectively precipitated by heating a suspension of the letrozole in a three-phase system (a letrozole solid phase and two liquid phases) from about 25° C. to about 60° C. (preferably to about 30° C.), and then allowing the suspension to cool, preferably to room temperature.

In another embodiment, the letrozole is purified by mixing letrozole containing isoletrozole and one or more additional impurities in an organic solvent, optionally with heating, to dissolve the letrozole; cooling to precipitate crystals of purified letrozole; isolating the crystals; optionally washing the crystals; and, optionally recrystallizing to further purify the letrozole. Suitable organic solvents for crystallizing the letrozole are selected from the group consisting of methanol, ethanol, n-propanol, isopropyl alcohol, n-butanol, sec-butanol, methyl acetate, ethyl acetate, isopropyl acetate, n-butyl acetate, isobutyl acetate, diisopropyl ether, methyl tert-butyl ether, acetonitrile, acetone, methyl ethyl ketone, diethyl ketone, methyl propyl ketone, methyl isobutyl ketone, and the like, and combinations thereof. Preferably, the solvent used for crystallizing the letrozole is selected from the group consisting of methanol, ethanol, isopropyl alcohol, methyl acetate, isopropyl acetate, methyl isobutyl ketone, diisopropyl ether, and combinations thereof.

Highly pure letrozole can be obtained by subjecting letrozole to one or more (e.g., successive) crystallizations in accordance with the present invention. For instance, highly pure letrozole can be obtained by subjecting the selectively precipitated product to two consecutive crystallizations from a suitable organic solvent. By way of further example, highly pure letrozole can be obtained by a processes, which comprises: mixing crude letrozole with a suitable organic solvent; optionally heating to an elevated temperature to dissolve the crude letrozole; gradually cooling to produce crystals of letrozole; filtering off the crystals, washing the crystals with an organic solvent; and, optionally, recrystallizing the letrozole crystals from an organic solvent.

The present invention provides a fast, simple and high-yield method of purifying letrozole under mild conditions, which can effectively remove isoletrozole and other impurities that may be produced in the synthesis of letrozole. The purification process of the invention can be used on an industrial scale, and avoids disadvantages associated with conventional processes such as, e.g., column chromatography. In accordance with the present invention, substantially pure letrozole can be obtained, e.g., letrozole having a purity of greater than about 95% by HPLC (e.g., letrozole having a purity of least about 98.5%, letrozole having a purity of at least about 99.5% by HPLC, letrozole having a purity of at least about 99.7% by HPLC, and the like) and/or letrozole containing isoletrozole at less than about 1 wt % (e.g., letrozole containing isoletrozole at less than about 0.5 wt %, letrozole containing isoletrozole at less than about 0.2 wt %, and the like). Accordingly, the present invention further provides highly pure letrozole, which can include, e.g.: (i) letrozole having a purity of least about 98.5% (e.g., letrozole having a purity of at least about 99.5% by HPLC, letrozole having a purity of at least about 99.7% by HPLC, and the like), (ii) letrozole containing isoletrozole at less than about 1 wt % (e.g., letrozole containing isoletrozole at less than about 0.5 wt %, letrozole containing isoletrozole at less than about 0.2 wt %, and the like), and (iii) combinations thereof, e.g., letrozole having a purity of at least about 98.5% (e.g., at least about 99.5%, at least about 99.7%, and the like) by HPLC and containing isoletrozole at less than about 1 wt %, (e.g., isoletrozole at less than about 0.5 wt %, isoletrozole at less than about 0.2 wt %, and the like).

The selective precipitation process of the present invention is simple and straight-forward, and can be conveniently carried out, e.g., by adding a mixture of water and a water-miscible solvent to a reaction mixture that already contains a water-immiscible solvent, a water-miscible solvent, or a mixture thereof. The selective precipitation process of the present invention is particularly advantageous in that there is no need to evaporate the solvent mixture in order to isolate the product (e.g., in substantially pure form) from the reaction mixture. In addition, is not necessary to filter salts such as, e.g., excess potassium carbonate, from the reaction mixture prior to performing the selective precipitation process, as the selective precipitation process itself can separate such salts from the product. As such, the selective precipitation process of the present invention can provide a substantial cost savings, e.g., in terms of time and energy, particularly when performed on a commercial scale.

The following examples further illustrate the invention but, of course, should not be construed as in any way limiting its scope.

EXAMPLE 1

This example demonstrates a method for preparing bromo-bis-(4-cyanophenyl)-methane.

A three-necked round-bottom flask equipped with a mechanical stirrer, a nitrogen inlet and a Dean Stark apparatus was charged with bis-(4-cyanophenyl)-methanol (60 g, 0.256 mole) and toluene (360 ml) and the reaction mixture was heated to 60° C. HBr (48%, 54 ml, 1.8 eq.) was added in one portion and the reaction mixture was refluxed for two hours, during which time water was removed by azeotropic distillation.

The reaction mixture was cooled to 70° C., water was added (250 ml), and stirring was maintained for 5 minutes. The two resulting layers were separated, the aqueous phase was washed with toluene (50 ml), and the organic layers were combined and washed with an aqueous solution of 5% potassium carbonate (200 ml), then with water (250 ml). Toluene was distilled off under reduced pressure (about 290 ml) and the solution was cooled to 40° C. Hexane was added (240 ml) and the mixture was cooled to room temperature and stirring was maintained for about 18 hours. The crude solid product was obtained by filtration (70.3 g) in 92% yield, having a purity of 99% (by HPLC).

EXAMPLE 2

This example demonstrates a method of preparing letrozole from bromo-bis-(4-cyanophenyl)-methane.

A round bottomed flask equipped with a thermometer, a mechanical stirring device and a nitrogen inlet tube was charged with triazole (29 g, 0.42 mole) and bromo-bis-(4-cyanophenyl)-methane (50 g, 0.168 mole). DMF (200 ml) and toluene (300 ml) were added, and the temperature was raised to 60° C. Potassium carbonate was added (23.2 g, 0.167 mole) and the temperature was raised to 80° C. under a nitrogen atmosphere and mixing was maintained at this temperature for about 1.5 hours. The reaction progress was checked by HPLC. After cooling to room temperature, acetic acid (20 ml) was added.

DMF (100 ml) and water (490 ml) were added to the reaction mixture to form a suspension (two liquid phases and a solid phase). After heating the suspension to 30° C. the resulting mixture was allowed to cool to room temperature. The resulting crystalline solid was washed with water (150 ml) and dried at 70° C. under reduced pressure to obtain crude dry letrozole (33.8 g, 70.5%, having a purity of 96% by HPLC, containing 3.5% isoletrozole).

EXAMPLE 3

This example demonstrates a method of preparing chloro-bis-(4-cyanophenyl)-methane.

A three-necked round-bottom flask equipped with a mechanical stirrer, a nitrogen inlet and a reflux condenser was charged with toluene (240 ml) and zinc chloride (34 g, 2 eq.). The mixture was stirred at 40° C. while HCl (37%, 60 ml, 5.64 eq.) was added in one portion, followed by the addition of bis-(4-cyanophenyl)-methanol (30 g, 0.128 mole). The reaction mixture was heated to 65° C. for 4 hours. Next, the reaction mixture was cooled to room temperature, water was added (60 ml), and stirring was maintained for 5 minutes. The two layers were separated and the organic phase was washed with an aqueous solution of 2.5% sodium carbonate (120 ml), then with water (60 ml). Toluene was distilled off under reduced pressure (about 180 ml) and the solution was cooled to 40° C. Hexane was added (120 ml) and the mixture was cooled to room temperature and stirring was maintained for about 0.5 hour. Then, the mixture was cooled to about 5° C. and stirring was maintained for additional 3 hours. The crude solid product was obtained by filtration (27.4 g) in 85% yield, having a purity of 98% (by HPLC).

EXAMPLE 4

This example demonstrates a method of preparing letrozole from chloro-bis-(4-cyanophenyl)-methane.

A round bottomed flask equipped with a thermometer, an mechanical stirring device and a nitrogen inlet tube was charged with triazole (17.4 g, 0.252 mole, 1.5 eq.) and chloro-bis-(4-cyanophenyl)-methane (42.2 g, 0.168 mole), followed by the addition of DMF (130 ml) and toluene (300 ml). The temperature was raised to 60° C., potassium carbonate was added (23.2 g, 0.167 mole) and the temperature was raised to 80° C. under anitrogen atmosphere, and mixing was maintained at this temperature during about 4 hours. The reaction progress was checked by HPLC. After cooling to room temperature, acetic acid (20 ml) was added.

DMF (100 ml) and water (490 ml) were added to reaction mixture to form a suspension (two liquid phases and a solid phase). After heating the suspension to 30° C., the resulting mixture was allowed to cool to room temperature. The resulting crystalline solid was washed with water (150 ml) and dried at 70° C. under reduced pressure to obtain crude dry letrozole (35.7 g, 74.4%).

EXAMPLE 5

This example demonstrates a method for purifying letrozole by crystallization from methanol.

A round bottomed flask was charged with letrozole (4.8 g) and methanol (about 48 ml) was added. The mixture was heated to about 60° C. to obtain a clear solution. The solution was gradually cooled to room temperature over about one hour. Then, the solution was cooled to about 2-5° C. for about 20 minutes. The crystals were obtained by filtration and washed with cold methanol (60 ml). The crystals were dried under vacuum to obtain crystallized letrozole (4.18 g, 87%) having a purity of 99.4% (containing 0.5% isoletrozole). The product was re-crystallized from methanol to obtain letrozole having a purity of 99.8% (containing 0.1% isoletrozole).

EXAMPLE 6

This example demonstrates methods of purifying letrozole by crystallization from specific solvents.

A typical experimental procedure is described, as follows. A small flask was charged with letrozole (0.47 g) and the solvent (about 7.5 ml) was added. The mixture was heated to obtain a clear solution. The mixture was gradually cooled to room temperature. Then, the solution was cooled to about 2-5° C. The resulting crystals were isolated by filtration and a sample of the crystallized letrozole was dissolved in acetonitrile and analyzed by HPLC. The purity profiles of letrozole obtained by crystallization of the precipitated product from different solvents are listed in Table 1.

TABLE 1

| | Solvent | Letrozole % peak area by HPLC | Isoletrozole % peak area by HPLC | Total other impurities, % peak area by HPLC |
|---|---|---|---|---|
| 1 | Methanol | 99.1 | 0.6 | 0.3 |
| 2 | Ethanol | 96.4 | 2.2 | 1.4 |
| 3 | Isopropyl alcohol | 94.4 | 3.0 | 2.6 |
| 4 | Methyl acetate | 97.3 | 2.0 | 0.7 |
| 5 | Isopropyl acetate | 96.3 | 3.3 | 0.4 |
| 6 | Methyl isobutyl ketone | 96.1 | 3.3 | 0.6 |
| 7 | Diisopropyl ether | 92.0 | 5.3 | 2.7 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for preparing letrozole, the method comprising the steps of:

reacting an activated bis-(4-cyanophenyl)-methane of the formula:

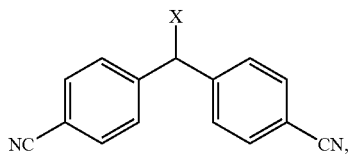

wherein X is a halogen or a sulfonate ester, with 1,2,4-triazole or a salt thereof in the presence of one or more water-immiscible organic solvents to produce a reaction mixture containing letrozole, and, as an impurity, isoletrozole;
  optionally adding an organic acid to the reaction mixture;
  adding water and at least one water-miscible solvent to the reaction mixture to produce a system comprising at least two liquid phases and at least one solid phase, wherein the solid phase comprises letrozole;
  heating the system and allowing the mixture to cool, to selectively precipitate letrozole;
  isolating the letrozole; and
  optionally subjecting the isolated letrozole to one or more crystallizations,
wherein the isolated and optionally crystallized letrozole has a purity of at least about 95% by HPLC and contains less than about 1 wt % isoletrozole.

2. The method of claim 1, wherein X is a halogen.

3. The method of claim 2, wherein X is a chlorine or a bromine.

4. The method of claim 3, wherein the compound of formula III is produced by a process comprising chlorinating bis-(4-cyanophenyl)-methanol, to produce a compound of formula III, wherein X is a chlorine.

5. The method of claim 3, wherein the compound of formula III is produced by a process comprising brominating bis-(4-cyanophenyl)-methanol, to produce a compound of formula III, wherein X is a bromine.

6. The method of claim 2, wherein the halo-bis-(4-cyanophenyl)-methane is isolated prior to reaction with 1,2,4-triazole or a salt thereof.

7. The method of claim 2, wherein the compound of formula III is produced by a process comprising reacting bis-(4-cyanophenyl)-methanol with an acid selected from hydrochloric acid, hydrobromic acid and combinations thereof, to produce the compound of formula III, wherein X is a chlorine or a bromine, and, optionally isolating the product.

8. The method of claim 7, wherein the acid is selected from the group consisting of hydrochloric acid and hydrobromic acid.

9. The method of claim 2, wherein the halo-bis-(4-cyanophenyl)-methane and 1,2,4-triazole or a salt thereof are reacted in the presence of at least one base and at least one organic solvent, to produce letrozole, and, as an impurity, isoletrozole.

10. The method of claim 9, wherein the base is selected from the group consisting of sodium hydroxide, potassium hydroxide, sodium carbonate, potassium carbonate, sodium bicarbonate, potassium bicarbonate, and combinations thereof.

11. The method of claim 1, wherein the water-miscible solvent is selected from the group consisting of acetonitrile, acetone, N,N-dimethylformamide (DMF), N,N-dimethylacetamide (DMA), dimethyl sulfoxide (DMSO), and combinations thereof.

12. The method of claim 1, wherein the reaction mixture comprises DMF and toluene.

13. The method of claim 1, wherein the reaction mixture is heated to from about 25° C. to about 60° C.

14. The method of claim 1, wherein the isolated letrozole is further subjected to one or more crystallizations from one or more solvents selected from methanol, ethanol, isopropyl alcohol, methyl acetate, isopropyl acetate, methyl isobutyl ketone, diisopropyl ether, and combinations thereof.

15. The method of claim 14, wherein the isolated letrozole is further subjected to one or more crystallizations from methanol.

16. The method of claim 14, wherein the isolated and crystallized letrozole has a purity of at least about 98.5% by HPLC.

17. The method of claim 14, wherein the isolated and crystallized letrozole contains isoletrozole at less than about 0.5 wt %.

* * * * *